United States Patent
Zhou

(10) Patent No.: US 8,217,153 B2
(45) Date of Patent: *Jul. 10, 2012

(54) METHODS AND SYSTEMS FOR ISOLATING TARGET MOLECULES FROM COMPLEX SOLUTIONS BY COLUMN-CHROMATOGRAPHY USING WASH SOLUTIONS CONTAINING ORGANIC SOLVENTS

(75) Inventor: Joe Xin Hua Zhou, Westlake, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,265

(22) Filed: Jan. 25, 2010

(65) Prior Publication Data

US 2010/0130727 A1    May 27, 2010

Related U.S. Application Data

(63) Continuation of application No. 11/650,292, filed on Jan. 5, 2007, now Pat. No. 7,834,162.

(60) Provisional application No. 60/757,049, filed on Jan. 6, 2006.

(51) Int. Cl.
*C07K 16/00* (2006.01)
*C07K 1/22* (2006.01)

(52) U.S. Cl. ........... 530/413; 530/391.1; 530/391.5

(58) Field of Classification Search ............ None
See application file for complete search history.

(56) References Cited

U.S. PATENT DOCUMENTS

| | | | |
|---|---|---|---|
| 5,310,688 A | 5/1994 | Zale et al. | |
| 6,870,034 B2 | 3/2005 | Breece et al. | |
| 6,946,075 B2 | 9/2005 | Kopf | |
| 7,223,848 B2 | 5/2007 | Coffman et al. | |
| 7,834,162 B2 * | 11/2010 | Zhou | 530/413 |
| 2002/0032317 A1 | 3/2002 | Blank | |
| 2003/0050450 A1 | 3/2003 | Coffman et al. | |
| 2003/0153735 A1 | 8/2003 | Breece et al. | |
| 2003/0201230 A1 | 10/2003 | Kopf | |
| 2010/0047228 A1 | 2/2010 | Scuderi et al. | |

OTHER PUBLICATIONS

Arakawa, Tsutomu, et al., Elution of Antibodies from a Protein—A Column by Aqueous Arginine Solutions, Protein Expression and Purification 36 (2004) 244-248.

Ejima, Daisuke, et al., Effective Elution of Antibodies by Arginine and Arginine Derivatives in Affinity Column Chromatography, Analytical Biochemistry 345 (2005) 250-257.

Hahn, Rainer, et al., Comparison of Protein a Affinity Sorbents, Journal of Chromatography B, 790 (2003) 35-51.

Sarciaux, Jeanne-Marie et al., Effects of Buffer Composition and Processing Conditions on Aggregation of Bovine IgG during Freeze-Drying, Journal of Pharmaceutical Sciences, vol. 88, No. 12 (Dec. 1999), 1354-1361.

Tsumoto, Kouhei, et al., Role of Arginine in Protein Refolding, Solubilization, and Purification, Biotechnol. Prog. (2004) 20, 1301-1308.

Conn et al., Outlines of Biochemistry, Fourth Edition, John Wiley & Sons, Inc. (1976) pp. 18-23.

* cited by examiner

*Primary Examiner* — David A Saunders
(74) *Attorney, Agent, or Firm* — John A. Lamerdin

(57) ABSTRACT

Various system and method embodiments of the present invention are directed to separating target molecules from complex solutions by affinity column chromatography using organic-solvent-containing eluants. In one embodiment of the present invention, an eluant containing an organic-solvent is used, at a first pH, to remove non-target solutes and suspended entities from an affinity chromatography column. The pH of the eluant is then changed to a second pH, and the organic-solvent-containing eluant is used to elute target molecules from the affinity column chromatography.

5 Claims, 3 Drawing Sheets

METHODS AND SYSTEMS FOR ISOLATING TARGET MOLECULES FROM COMPLEX SOLUTIONS BY COLUMN-CHROMATOGRAPHY USING WASH SOLUTIONS CONTAINING ORGANIC SOLVENTS

CROSS-REFERENCE TO RELATED APPLICATION

This application is a continuation of U.S. application Ser. No. 11/650,292 filed Jan. 5, 2007, now U.S. Pat. No. 7,834,162, which claims the priority benefit of U.S. Provisional Patent Application No. 60/757,049 file Jan. 6, 2006.

TECHNICAL FIELD

The present invention is related to column chromatography, and, in particular, to purification of target molecules by column chromatography using eluants that contain organic solvents.

BACKGROUND OF THE INVENTION

Column chromatography is a commonly used technique for purification of particular types of molecules from complex sample solutions and complex sample mixtures that include solutes and suspended or partially solvated chemical entities, such as membrane fragments. A chromatography column is prepared by suspending a resin in a buffer solution to form a resin slurry, and then packing the resin slurry within a chromatography tube to form a matrix within the chromatography tube by following a packing procedure, or packing mode. The matrix constitutes the solid phase or stationary phase within the chromatography column. A complex solution that contains one or more types of molecules to be purified, each type referred to as a "target molecule," is loaded onto the chromatography column in which buffer conditions are established to promote separation of the one or more target molecules from the complex solution. A buffer solution, or mobile phase, is then directed through the chromatography column to move desired target molecules and undesired sample-solution components through the chromatography column. Different types of solutes move through the chromatography column at different rates, depending on their different mobilities in, and different affinities for, the mobile phase and the stationary phase, resulting in separation of the one or more target molecules from solutes and suspended entities present in the original sample solution. Solutions containing the one or more target molecules, referred to as "eluates," are subsequently eluted from the chromatography column.

Column chromatography systems are frequently used for purifying biomolecules, including proteins and other biopolymers, from complex solutions and mixtures, such as, for example, purifying recombinant proteins from cell lysates and cell filtrates. Although column chromatography is commonly used to purify antibody target molecules, certain problems are frequently encountered. It can be difficult to maintain desired pH ranges, during chromatography-based purification procedures, which preserve the integrity of the antibody target molecules. In certain cases, adsorption of non-target solutes to the column-chromatography matrix may decrease the resolution, yield, and/or purity of the antibody target molecule. As a result, researchers, pharmaceutical manufacturers, chromatography-column and matrix manufacturers and vendors, and users of chromatography-based purification methods have recognized the need for improved chromatography-based purification methods that preserve desired pH ranges.

SUMMARY OF THE INVENTION

Various system and method embodiments of the present invention are directed to separating target molecules from complex solutions by affinity column chromatography using organic-solvent-containing eluants. In one embodiment of the present invention, an eluant containing an organic-solvent is used, at a first pH, to remove non-target solutes and suspended entities from an affinity chromatography column. The pH of the eluant is then changed to a second pH, and the organic-solvent-containing eluant is used to elute target molecules from the affinity column chromatography.

DETAILED DESCRIPTION

Figure 1:
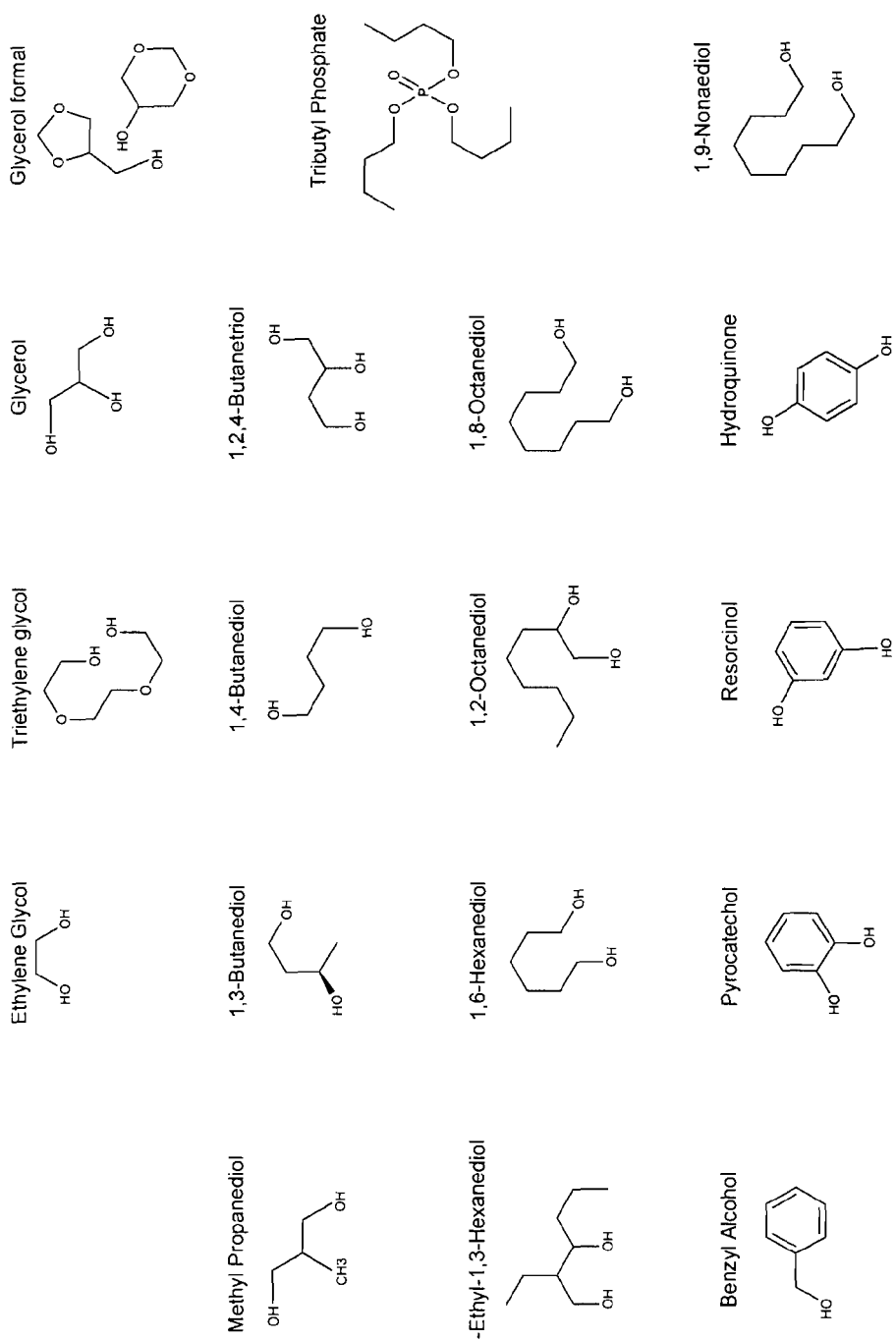
FIG. 1 shows chemical structures of a number of organic solvents that are used in eluants according to various embodiments of the present invention.

Various embodiments of the present invention are directed to systems and methods for purifying target molecules, including antibodies and other biopolymers, by affinity chromatography using eluants that contain organic solvents. These embodiments are described, below, following a description of the column chromatography systems in which method embodiments of the present invention may be practiced and a description of a number of organic solvents suitable for the organic-solvent-containing eluants used in method embodiments of the present invention.

Chromatography-Based-Process Context

A chromatography column may be used for any of many different liquid chromatographic processes, including ion-exchange chromatography, size-exclusion chromatography, hydrophobic interaction chromatography, and affinity chromatography. In ion-exchange chromatography, a target molecule is separated from a complex solution or mixture based on electrostatic forces between charged functional groups of target molecules and charged functional groups of the chromatography-column matrix. Cation-exchange resins have negatively charged functional groups that attract positively charged functional groups of target molecules, and anion-exchange resins have positively charged functional groups that attract negatively charged functional groups of target molecules. Molecules bound through electrostatic forces to the matrix can be eluted by increasing the ionic strength of the buffer solution within the chromatography column over time. In affinity chromatography, a target molecule, such as an antibody, is separated from a complex solution based on the affinity of the target molecule for a ligand or ligand-binding entity that is covalently bound to the matrix. Molecules in the complex solution or mixture with weak affinity, or lacking affinity, for the ligand or ligand-binding entity flow through the chromatography column unimpeded, leaving the target molecule bound to the matrix. The target molecule can then be eluted from the chromatography column by altering buffer conditions to decrease the affinity of the target molecule for the ligand or ligand-binding entity.

Protein A is a ~41 kDa protein from *Staphylococcus aureas* that binds with high affinity (~$10^{-8}$ M-$10^{-12}$ M to human IgG) to the $C_H2/C_H3$ domain of the Fc regions of antibodies and is therefore commonly immobilized within an affinity-chromatography matrix for purifying target antibodies. In addition, other types of hybrid target molecules containing Fc regions, or portions of Fc regions, bound by protein A can be purified by protein-A-based affinity chromatography. Antibody target molecules and other types of Fc-containing or Fc-portion-containing target molecules bound by protein A are collectively referred to as "protein-A-selected target molecules." Due to the biochemical properties of protein A, including a lack of disulfide bond linkages, protein A is very stable and can be used with high salt conditions and/or denaturants, such as 10 M urea, 6 M guanidine, and 80 mM dithiothreitol. Protein-A affinity chromatography is often used for purification of monoclonal antibodies and fusion proteins containing the antibody constant fragment Fc. About 98% of process impurities, including viral particles, can be removed by protein-A affinity column chromatography in a single step, with high product yields.

There are many commercially available protein-A affinity chromatography resins that may be used for antibody purification, including ProSep® controlled-pore glass resins produced by Millipore and MabSelect™ cross-linked agarose resin products produced by GE Healthcare, formerly Amersham Biosciences. Both MabSelect and ProSep resins have dynamic binding capacities approaching greater than 20 g/L, linear flow velocities for producing commercial quantities of antibodies ranging from 200 to 600 cm/hr, and pH stabilities from about 2 to about 10. Both types of resin are chemically stable when exposed to urea and other reducing agents.

Several problems are encountered in using affinity chromatography for purifying Fc-containing target molecules. A first problem is that certain non-target molecules, such as Chinese Hamster Ovary Proteins ("CHOP"), may remain bound to the protein-A resin, despite a first elution step in which eluant is passed through the affinity chromatography column to remove the CHOP. A second problem concerns relatively harsh conditions that may be used, in current methods, for eluting Fc-containing target molecules. Both glass- or-silica-based protein-A resin and agarose-based protein-A resins have high affinities for Fc-containing target molecules. Increasing the ionic strength of an eluant is often insufficient to release the antibody from protein-A resin. Instead, an eluant with a low pH (~2.5-3.5) is typically used to release the Fc-containing target molecules from chromatography columns prepared with protein-A affinity-chromatography resins. However, antibodies and other Fc-containing proteins or hybrid polymers may not be stable under these low pH conditions. When low pH elution conditions are used, a significant portion of an eluted target molecule may be partially unfolded and/or aggregated, thus decreasing the yield of properly folded, active target molecules and increasing the difficulty of purifying the properly folded, active target molecules.

Organic Solvents Suitable for Eluants Used in Method Embodiments of the Present Invention FIG. 1 shows chemical structures of a number of organic solvents that are used in various embodiments of the present invention. These organic solvents include: (1) methyl propanediol; (2) 2-ethyl-1,3-heaxanediol; (3) benzyl alcohol; (4) ethylene glycol; (5) 1,3-butanediol; (6) 1,6-heaxanediol; (7) pyrocatechol; (8) triethylene glycol; (9) 1,4-butanediol; (10) 1,2-octanediol; (11) resorcinol; (12) glycerol; (13) 1,2,4-butanetriol; (14) 1,8-octanediol; (15) hydroquinone; (16) glycerol formal (a 3:4 mixture of 4-hydroxymethyl-1,3-dioxolane and 5-hydroxy-1,3-dioxane); (17) tributyl phosphate; and (18) 1,9-nonaediol. These organic solvents are representative of a class of oxygen-containing organic solvents have been found to provide good target-molecule separation results when used in eluants for affinity-column-chromatography-based purification processes. The compounds show certain common features: (1) they are soluble in water; (2) they generally have at least 2 oxygen atoms available for hydrogen bonding with water, or have a ratio of oxygen atoms to carbon atoms greater than, or equal; to, 1:7; (3) they have at least 2 alkyl or aryl carbons; (4) they have relatively low molecular weights; and, (5) they may be used as both impurity-removing eluants and as target-molecule eluants. In general, eluant and washing solutions used in methods of the present invention contain, in a first set of embodiments, between 5% and 60%, by volume, of an organic solvent. In a second set of embodiments, eluant and washing solutions contain between 5% and 50%, by volume, of an organic solvent. In a third set of embodiments, eluant and washing solutions contain between 5% and 30%, by volume, of an organic solvent. In a fourth set of embodiments, eluant and washing solutions contain between 5% and 20%, by volume, of an organic solvent. In a fifth set of embodiments, eluant and washing solutions contain between 10% and 60%, by volume, of an organic solvent. In a sixth set of embodiments, eluant and washing solutions contain between 20% and 60%, by volume, of an organic solvent. In a seventh set of embodiments, eluant and washing solutions contain between 30% and 55%, by volume, of an organic solvent. In an eighth set of embodiments, eluant and washing solutions contain between 35% and 45%, by volume, of an organic solvent. In a ninth set of embodiments, eluant and washing solutions contain between 10% and 20%, by volume, of an organic solvent. In a tenth set of embodiments, eluant and washing solutions contain between 20% and 30%, by volume, of an organic solvent. In an eleventh set of embodiments, eluant and washing solutions contain between 30% and 40%, by volume, of an organic solvent.

DESCRIBED EMBODIMENTS OF THE PRESENT INVENTION

Figure 2:
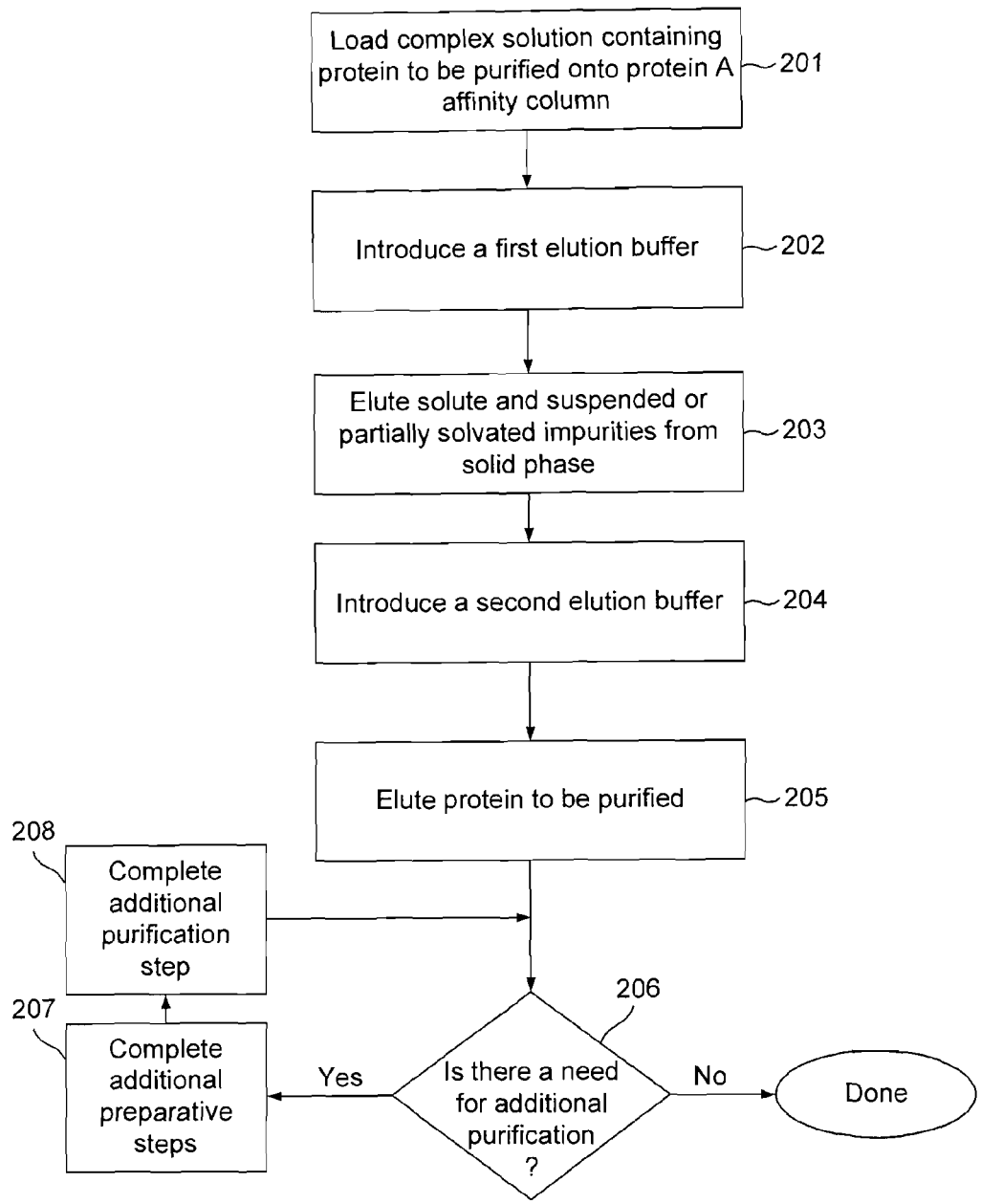
FIG. 2 shows a flow diagram representing one of many method embodiments of the present invention.

FIG. 2 shows a flow diagram representing one of many method embodiments of the present invention. The described method comprises an iterative protein-purification procedure. In step 201, a complex solution containing an antibody or Fc-containing target protein is loaded onto a chromatography column prepared with a protein-A affinity-chromatography resin. The protein-A resin present in the affinity chromatography column may be a glass-based resin, such as ProSep-vA™, an agarose-based resin, such as MabSelect™, or another type of protein-A affinity-chromatography resin. In step 202, a first organic-solvent-containing eluant is introduced into the chromatography column. In step 203, non-target solutes and suspended or partially solvated impurities are eluted from the solid phase of the chromatography column. The target protein is retained in the solid phase of the chromatography column. In step 204, a second organic-solvent-containing eluant is introduced into the chromatography column. The second eluant decreases the affinity of the target protein for the protein-A resin. In step 205, the target protein is eluted from the chromatography column. If no additional purification is needed, as determined in step 206, the purification method is complete. If additional purification is needed, as determined in step 206, additional preparative steps are carried out in step 207 in order to prepare for additional purification steps carried out in step 208.

In one embodiment of the present invention, a glycerol-formal-containing eluant is used as both the first organic-solvent-containing eluant as well as the second organic-solvent-containing eluant in the above-described method. Prior to step 202, the glycerol-formal-containing eluant is adjusted to have a pH sufficiently high to remove non-target solutes and suspended or partially solvated impurities without releasing bound target protein. Prior to step 204, the glycerol-formal-containing eluant is adjusted to have a pH sufficiently low to release bound target protein. Thus, a single organic-solvent-containing eluant can serve both to remove non-target solutes and suspended or partially solvated impurities as well as to elute target molecules, simplifying the target-molecule-purification process.

The first and second eluants are introduced into the chromatography column to facilitate migration of chemical entities within the mobile phase. The eluants may contain buffers to resist changes in pH. In one embodiment of the present invention, the first eluant contains an organic solvent of the class of organic solvents described above. The first eluant may facilitate separation of impurities, such as DNA and CHOP, from the target protein. In a second embodiment of the present invention, the second eluant contains an organic solvent of the class of organic solvents described above. The second eluant facilitates release of the target protein from the chromatography column into the mobile phase at a higher pH than would be possible by using standard eluants that do not contain organic solvents. The target protein may, at any suitable step in the purification process, be collected, concentrated, titrated to a suitable pH and conductivity, and subjected to a further purification step, such as column chromatography using a chromatography column prepared with Fractogel® COO⁻ cation-exchange-chromatography resin produced by Merck KGA. In various embodiments of the present invention, the same organic solvent is employed in both the first and second eluants, with impurity removal carried out at a relatively neutral pH of between 6.5 and 8.0, and antibody elution carried out at a relatively lower pH of between 4.0 and 5.0, so that, by simply changing the pH of the eluant, both impurity removal and antibody elution can be carried out using essentially the same eluant solution.

EXAMPLE 1

In order to test the ability of an organic-solvent-containing eluant to increase CHOP clearance from a glass-based protein-A resin, chromatography columns prepared with ProSep-vA resin were loaded with a heterogeneous-mixture sample containing a monoclonal antibody and washed with various wash solutions. An agarose-based protein-A resin (MabSelect™), which is known to have a satisfactory level of CHOP clearance (<5000 ppm CHOP remaining) was included as a positive control and a "no wash" condition was included as a negative control, respectively, for assaying CHOP clearance. Concentrations of CHOP, DNA, and mobilized protein A were calculated by measuring UV absorbance for each component. The data in Table 1 summarizes the results.

TABLE 1

CHOP Clearance and DNA Clearance of a Glass-Based Protein-A-Resins Using Organic-Solvent-Containing Eluants.

| | Load | ProSep-vA | | | | MabSelect |
| --- | --- | --- | --- | --- | --- | --- |
| | | No wash | Eluant 1 | Eluant 2 | Eluant 3 | No Wash |
| CHOP (ppm) | 410,943 | 8,367 | 1,367 | 1,440 | 497 | 2000 |
| DNA (ppm) | 13,054,830 | NA | 0.089 | 0.093 | 0.071 | 1.641 |
| Unbound Protein A (ppm) | NA | 14.3 | 17.1 | 14.1 | 12.6 | 14.9 |

Eluant 1 is 2-methyl-1,3-propanediol (20%), 0.5 M NaCl.
Eluant 2 is butanediol (20%), 0.5 M NaCl.
Eluant 3 is glycerol formal (20%), 0.5 M NaCl.
The term "No Wash" refers to continuous flow of an equilibration buffer.
The term "NA" refers to not measured and/or not recorded.

A comparison of CHOP levels in the sample load and main pool of MabSelect™ indicate that CHOP levels were reduced by 2.2 logs using an agarose-based protein-A resin, decreasing the measured CHOP level from >410,000 ppm to 2000 ppm. When CHOP clearance of the chromatography column prepared with MabSelect™ and the CHOP clearance of the chromatography column prepared with ProSep-vA™ in the absence of a wash solution were compared, the MabSelect-containing chromatography column had a 4-fold lower level of CHOP (2,000 vs. >8,000). However, when the ProSep-containing chromatography column was washed with an organic-solvent-containing eluant, the CHOP clearance and DNA clearance was greater than that observed with the unwashed MabSelect-based chromatography column. The relative equivalence of unbound protein A observed in the mobile phase of the samples indicates that the various organic-solvent-containing eluants tested do not substantially increase the dissociation of protein A from the backbone matrix. The results of Example 1 illustrate that organic-solvent-containing eluants are able to effectively remove impurities from the solid phase of a glass-based protein-A resin.

EXAMPLE 2

Figure 3A:
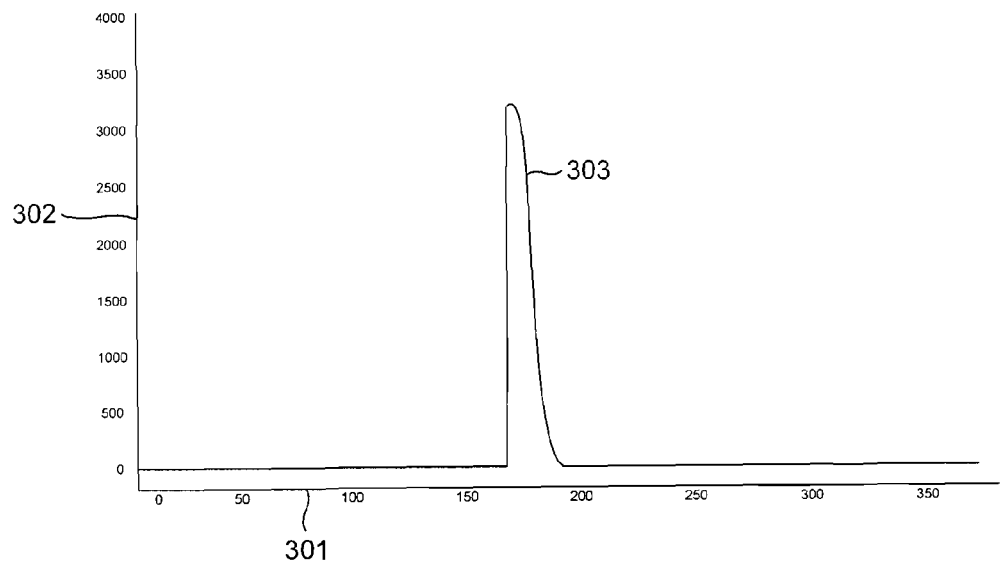
FIGS. 3A-B illustrate antibody elution-versus-time plots for an organic-solvent-containing eluant that represents an embodiment of the present invention.
Figure 3B:
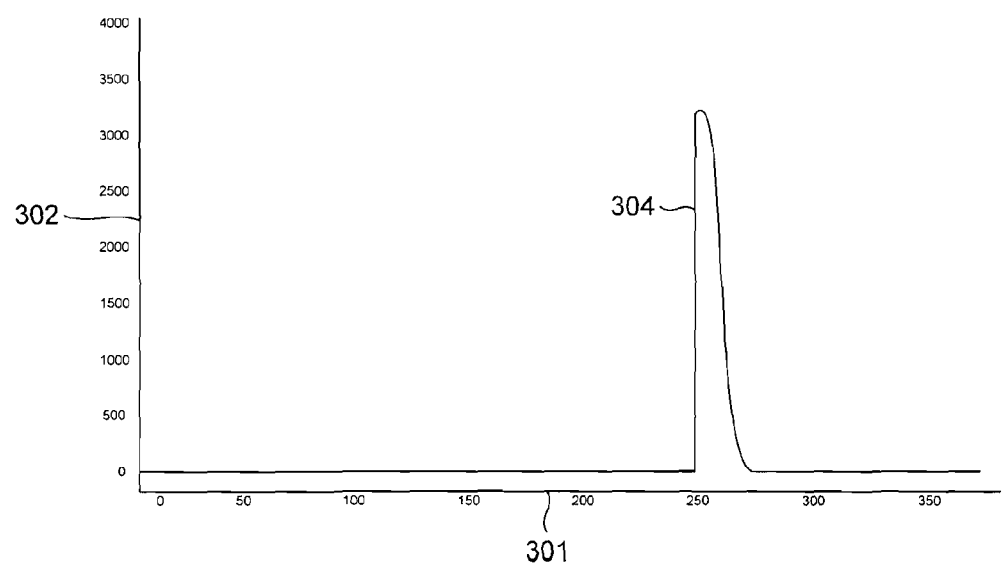

FIGS. 3A-B illustrate antibody elution-versus-time plots for an organic-solvent-containing eluant that represents an embodiment of the present invention. The x axis 301 of each graph indicates the retention time. The y axis 302 of each graph indicates UV absorbance, which provides a measure of protein concentration. Curves 303 and 304 indicate the elution profiles of antibodies eluted from a protein-A-based affinity chromatography column and a cation-exchange chromatography column, respectively. In order to test the use of organic-solvent-containing eluants for eluting an adsorbed antibody from the solid phase of a protein-A-based affinity chromatography column into the mobile phase, a monoclonal antibody was loaded onto a chromatography column prepared with MabSelect™ and equilibrated with a loading buffer of 20 mM 2-amino-2-hydroxymethyl-1,3-propanediol ("Tris") and 100 mM NaCl, pH 7.4. As shown in FIG. 3A, the antibody peak appeared after washing the MabSelect-based chromatography column with a wash buffer containing 20% glycerol formal at pH 4.5. Only a small protein peak was observed after a further elution with an eluant having a pH of 3.4, indicating that the majority of adsorbed antibody was eluted with the pH 4.5 glycerol formal-containing buffer. The eluted antibody from the MabSelect-based chromatography column was then loaded and adsorbed to a Fractogel-COO$^-$-based cation-exchange chromatography column at a capacity of 45 g/L and pH 5.0. As illustrated in FIG. 3B, the antibody eluted from the Fractogel-COO$^-$-based chromatography column using 13 column volumes of a pH 5.0-6.0 salt gradient. No protein A was observed eluting from the Fractogel-COO$^-$-based chromatography column during the pre-elution wash step, indicating that glycerol formal at the test concentration of 20% does not disrupt protein A binding to the matrix backbone. The same elution profile was observed when ProSep-vA, rather than MabSelect, was used. The results of Example 2 indicate that an organic-solvent-containing eluant is capable of eluting an antibody from a protein-A-based affinity chromatography column in a discrete peak for subsequent loading onto another chromatography column for further purification. In addition, the efficient binding of antibody eluted from the protein-A-based chromatography column to the Fractogel-COO$^-$-based chromatography-column matrix indicates that the binding domains of the antibody are generally intact. Additional analysis by circular dichroism and Fourier-transform infrared spectroscopy showed that the antibody eluted from the protein-A-based chromatography column to the Fractogel-COO$^-$-based chromatography-column has a near-native conformation.

Although the present invention has been described in terms of particular embodiments, it is not intended that the invention be limited to these embodiments. Modifications within the spirit of the invention will be apparent to those skilled in the art. For example, in an alternate embodiment of the present invention, the organic solvent may contain additional functional groups and/or atoms other than oxygen, hydrogen, carbon, and phosphorous. The organic solvent may be chemically modified during the purification process or become bonded to one or more molecules during the purification process. One or more organic solvents may be present in one or more of the eluants used. The eluants used during the purification process may contain ions and other solutes in addition to those listed in the above description. The organic-solvent-containing eluants may be used in any suitable liquid column chromatography process, including cation-exchange chromatography, anion-exchange chromatography, size-exclusion chromatography, and hydrophobic-interaction chromatography. The organic-solvent-containing eluants may be used in any suitable liquid column chromatography system, including fast performance liquid chromatography, high performance/high pressure liquid chromatography, and low pressure liquid chromatography. Although the described embodiments are employed in protein-purification processes, organic-solvent-containing eluants may be employed in purification processes directed to purification of other target molecules, including other types of biopolymers.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to explain the principles of the invention and its practical applications, to thereby enable others skilled in the art to best utilize the invention and various embodiments with various modifications as are suited to the particular use contemplated.

The invention claimed is:

1. A method for purifying protein-A-selected target molecules from a complex solution by affinity column chromatography, the method comprising:
   (a) loading the complex solution onto a protein A-based affinity-column-chromatography column;
   (b) adsorbing the protein-A-selected target molecules to an affinity-column-chromatography matrix having protein-A bound thereto within the protein A affinity-column-chromatography column;
   (c) the chromatography column with a wash solution comprising between 5% and 60% by volume of one or more of the organic solvents methyl propanediol, 2-ethyl-1,3-hexanediol, benzyl alcohol, ethylene glycol, 1,3-butanediol, 1,6-hexanediol, pyrocatechol, triethylene glycol, 1,4-butanediol, 1,2-octanediol, resorcinol, glycerol, 1,2,4-butanetriol, 1,8-octanediol, hydroquinone, 4-hydroxymethyl-1,3-dioxolane, 5-hydroxy-1,3-dioxane, tributyl phosphate, and 1,9-nonaediol, the wash solution maintained at a pH of between 6.5 and 8.0; and
   (d) eluting the target antibody molecules by using an eluant.

2. The method of claim 1 wherein the eluant is maintained at a pH of between 4.0 and 5.0.

3. The method of claim 1 wherein the eluent further includes between 100 mM and 0.5 M NaCl.

4. The method of claim 1 wherein the eluant and organic-solvent-containing wash solution differ in pH but contain the same organic solvent.

5. The method of claim 1 wherein the wash solution further includes between 100 mM and 0.5 M NaCl and between 10 mM and 50 mM Tris.

* * * * *